United States Patent [19]

Böger et al.

[11] 4,404,225
[45] Sep. 13, 1983

[54] THIOUREA DERIVATIVES HAVING PESTICIDAL ACTIVITY

[75] Inventors: Manfred Böger, Weil am Rhein, Fed. Rep. of Germany; Jozef Drabek, Oberwil, Switzerland

[73] Assignee: Ciba-Geigy Corporation, Ardsley, N.Y.

[21] Appl. No.: 270,755

[22] Filed: Jun. 5, 1981

Related U.S. Application Data

[63] Continuation of Ser. No. 164,375, Jun. 30, 1980, abandoned.

[30] Foreign Application Priority Data

Jul. 3, 1979 [CH] Switzerland ........................ 6197/79
Jun. 11, 1980 [CH] Switzerland ........................ 4490/80

[51] Int. Cl.$^3$ ..................... C07C 157/09; A01N 47/30
[52] U.S. Cl. ...................................... 424/322; 564/28; 564/52
[58] Field of Search ..................... 564/28, 52; 424/322

[56] References Cited

U.S. PATENT DOCUMENTS

| | | | |
|---|---|---|---|
| 2,723,192 | 11/1955 | Todd ................................. | 564/52 X |
| 3,119,682 | 1/1964 | Martin et al. ..................... | 564/52 X |
| 3,781,290 | 12/1973 | Spaun et al. ...................... | 564/28 X |
| 3,799,759 | 3/1974 | Martin et al. ..................... | 564/28 X |
| 3,933,814 | 1/1976 | Haberkorn et al. .............. | 564/28 X |
| 4,080,193 | 3/1978 | Rohe et al. ....................... | 564/52 X |
| 4,087,272 | 5/1978 | Rohe et al. ....................... | 564/52 X |

FOREIGN PATENT DOCUMENTS 2730620 1/1979 Fed. Rep. of Germany .

OTHER PUBLICATIONS

Spaun et al., CA 77:48078y (1972).

*Primary Examiner*—Thomas A. Waltz
*Attorney, Agent, or Firm*—Frederick H. Rabin

[57] ABSTRACT

Compounds of the formula I and II

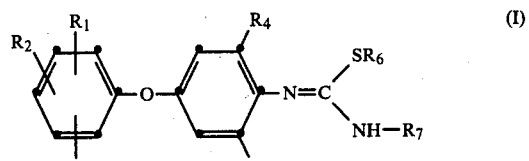

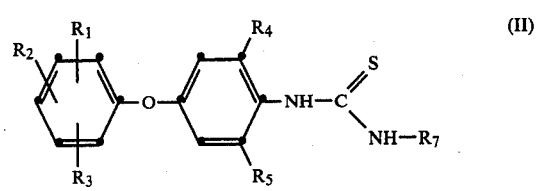

wherein $R_1$, $R_2$ and $R_3$ independently of one another are each hydrogen, $C_1$–$C_4$-alkyl, methoxy, halogen, trifluoromethyl or nitro, $R_4$ is hydrogen or methyl, $R_5$ is $C_1$–$C_3$-alkyl, $R_6$ is $C_1$–$C_6$-alkyl, $C_2$–$C_6$-aklenyl, $C_3$–$C_5$-alkynyl, $C_3$–$C_6$-cycloalkyl, $C_2$–$C_4$-(alkoxyalkyl) or $C_2$–$C_4$-(alkylthioalkyl), and $R_7$ is $C_1$–$C_{12}$-alkyl, $C_3$–$C_5$-alkenyl or $C_3$–$C_8$-cycloalkyl, and the acid addition salts of compounds of the formulae I, are novel. The compounds of the formula II can be used as starting materials for producing compounds of the formula I. The mentioned compounds of the formulae I and II have a pesticidal action, especially an acaricidal and insecticidal action, and are particularly effective against plant pest

18 Claims, No Drawings

THIOUREA DERIVATIVES HAVING PESTICIDAL ACTIVITY

This is a continuation of application Ser. No. 164,375 filed on June 30, 1980, now abandoned.

The present invention relates to novel thiourea derivatives having pesticidal activity, to processes for producing them, to pesticidal compositions which contain these compounds as active ingredients, and to processes for combating pests by application of the novel compounds.

N-Phenyl-N'-alkyl-S-alkyl-isothioureas having pesticidal properties are known (cp. German Offenlegungsschrift No. 2,730,620). There are provided by the present invention novel thiourea derivatives which are highly effective against pests, particularly against representatives of the order Acarina, and against insects, and which, by virtue of their advantageous biological properties, are especially suitable for practical application.

The novel substituted N-phenoxyphenyl-isothioureas provided by the invention correspond to the formula I

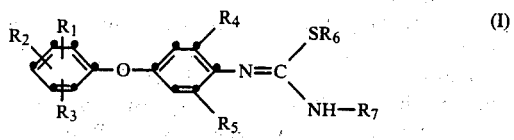

wherein $R_1$, $R_2$ and $R_3$ independently of one another are each hydrogen, $C_1$–$C_4$-alkyl, methoxy, halogen, trifluoromethyl or nitro, $R_4$ is hydrogen or methyl, $R_5$ is $C_1$–$C_3$-alkyl, $R_6$ is $C_1$–$C_6$-alkyl, $C_2$–$C_6$-alkenyl, $C_3$–$C_5$-alkynyl, $C_3$–$C_6$-cycloalkyl, $C_2$–$C_4$-(alkoxyalkyl) or $C_2$–$C_4$-(alkylthioalkyl), and $R_7$ is $C_1$–$C_{12}$-alkyl, $C_3$–$C_5$-alkenyl or $C_3$–$C_8$-cycloalkyl.

Alkyl or alkenyl and alkynyl groups in the formula I can be branched-chain or straight-chain. By "halogen" are meant chlorine, fluorine, bromine and iodine, preferably chlorine.

The compounds of the formula I can occur in the form of addition salts of inorganic or organic acids, and can be used according to the invention also in the form of their salts. The term 'compounds of the formula I' is accordingly to be understood as embracing within the scope of the present invention both the free compounds of the formula I and the acid addition salts thereof.

The compounds of the formula I can be converted into their acid addition salts by procedures known per se. Suitable for forming addition salts are for example: hydrochloric acid, hydrobromic acid, hydriodic acid, nitric acid, phosphoric acid, sulfuric acid, acetic acid, propionic acid, butyric acid, valeric acid, oxalic acid, malonic acid, succinic acid, malic acid, maleic acid, fumaric acid, lactic acid, tartaric acid, citric acid, benzoic acid, phthalic acid, cinnamic acid and salicyclic acid.

The compounds of the formula I are produced analogous to known processes, which comprises for example reacting a thiourea of the formula II

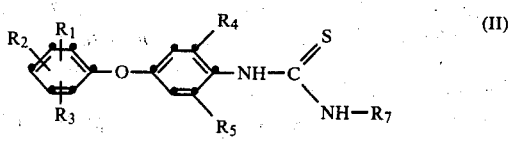

with a halide of the formula III

the radicals $R_1$ to $R_7$ in the formulae II and III having the meanings already defined under the formula I, and "Hal" denoting a halogen atom, particularly a chlorine or bromine atom.

The above process is performed advantageously at a temperature of between 0° and 100° C., under normal or slightly elevated pressure, and preferably in the presence of a solvent or diluent inert to the reactants. Suitable solvents or diluents are for example: ethers and ethereal compounds, such as diethyl ether, diisopropyl ether, dioxane and tetrahydrofuran; aromatic hydrocarbons, such as benzene, toluene and xylenes; ketones, such as acetone, methyl ethyl ketone and cyclohexanone; alcohols and dimethylformamide.

The compounds of the formula II to be used as starting materials for the process described in the foregoing are novel and likewise form subject matter of the invention. They can be readily obtained from known precursors by reacting for example an isothiocyanate of the formula IV

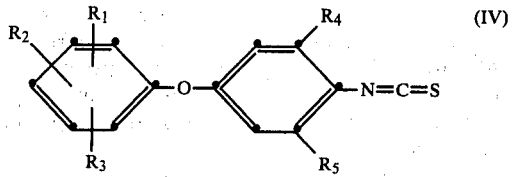

with an amine of the formula V

where $R_1$ to $R_5$ inclusive and $R_7$ in the formulae IV and V have the meanings already defined.

The process for producing compounds of the formula II is preferably performed is the presence of a solvent or diluent inert to the reactants, at a reaction temperature of 0° to 100° C. under normal pressure. Solvents and diluents suitable for this process are the substances already mentioned for the process for producing compounds of the formula I.

It has now been found that surprisingly the compounds of the formulae I and II according to the invention exhibit a particularly strong action against acarids which damage plants (mites: for example of the families: Tetranychidae, Tarsonemidae, Eriophydae, Tyroglyphidae and Glycyphagidae), and also against ectoparasitic acarids (mites and ticks; for example of the families: Ixodidae, Argasidae, Sarcoptidae and Dermanyssidae), which infest productive animals. Some of the compounds according to the invention are distinguished by a good acaricidal-ovicidal activity and leaf-penetration action. The compounds according to the invention are suitable in particular for combating the following species of mites which infest fruit and vegetable crops: *Tetranychus urticae, Tetranychus cinnabarinus, Panony-* chus ulmi, Bryobia rubrioculus, Panonychus citri, Eriophyes pyri, Eriophyes ribis, Eriophyes vitis, Tarsomemus pallidus, Phyllocoptes vitis and Phyllocoptura oleivora.

Furthermore, it has been established that the compounds of the formulae I and II also have marked insecticidal properties, and accordingly are particularly suitable for combating plant-damaging and ectoparasitic insects, for example of the orders: Lepidoptera, Coleoptera, Heteroptera, Diptera, Orthoptera and Homoptera. The compounds according to the invention are especially suitable for combating aphids and other insects which damage plants by eating in crops of ornamental plants and productive plants, for example *Spodoptera littoralis* and *Heliothis virescens*.

Compounds of the formulae I and II according to the invention which are preferred on account of their effectiveness are those wherein $R_1$ and $R_2$ independently of one another are each hydrogen, methyl, chlorine, trifluoromethyl, methoxy or nitro, $R_3$ is hydrogen, $R_4$ is hydrogen or methyl, and $R_5$ is methyl. Of importance are also those compounds of the formulae I and II wherein $R_2$ is hydrogen or chlorine, and also those in which the radical $R_1$ is in the 4-position. To be emphasised by virtue of their good pesticidal action are moreover the compounds of the formulae I and II which are characterised in that $R_7$ is $C_1$-$C_4$-alkyl, preferably tert-butyl. Also preferred are compounds of the formula I wherein $R_6$ is $C_1$-$C_4$-alkyl, preferably methyl or ethyl.

The compounds of the formulae I and II are used according to the invention on their own, or they form an active component in compositions which contain also suitable customary carriers or additives, or mixtures of substances of this kind. Suitable carriers and additives can be solid or liquid and they correspond to the substances common in formulation practice, such as natural or regenerated substances, solvents, dispersing agents, wetting agents, adhesives, thickeners, binders and/or fertilisers.

The insecticidal and acaricidal action of the compositions according to the invention can be considerably broadened by the addition of other acaricides and/or insecticides. Suitable additives are for example: organic phosphorus compounds; nitrophenols and derivatives thereof; formamidines; ureas; pyrethrin-like compounds; and carbamates and chlorinated hydrocarbons.

The compositions according to the invention can be in the form of dusts, granulates, dispersions, solutions and suspensions, as well as in the form of water-dispersible wettable powders, pastes, emulsions and emulsion concentrates, and can be applied in this form.

The content of active substance (compounds of the formula I or II) in the compositions described above is between 0.1 and 95%; it is to be mentioned in this respect that with application from an aeroplane, or by means of other suitable application devices, also higher concentrations can be used.

The compounds of the formula I can be formulated for example as follows:

EMULSION CONCENTRATE I 20 parts by weight of the active substance are dissolved in
70 parts by weight of xylene, and to the solution are added
10 parts by weight of an emulsifying agent consisting of a mixture of an arylphenylpolyglycol ether and the calcium salt of dodecylbenzenesulfonic acid.

Water can be added in any proportion to the emulsion concentrate to form a milky emulsion.

EMULSION CONCENTRATE II 5 to a maximum of 30 parts by weight of active substance are dissolved at room temperature with stirring in
30 parts by weight of dibutylphthalate,
10 parts by weight of Solvent 200 (low-viscous, highly aromatic petroleum distillate),
15 to 35 parts by weight of Dutrex 238 FC (viscous highly aromatic petroleum distillate), and to the solution are added
10 parts by weight of an emulsifier mixture consisting of castor-oil polyglycol ether and the calcium salt of dodecylbenzenesulfonic acid.

The emulsion concentrate thus obtained produces milky emulsions when water is added.

WETTABLE POWDER 5 to 30 parts by weight of the active substance are thoroughly mixed, in a mixing apparatus, with
5 parts by weight of an absorbing carrier material (Kieselsäure K 320 [silicic acid] or Wessalon S) and
55 to 80 parts by weight of a carrier material (bolus alba or Kaolin B 24) and a dispersing agent mixture consisting of
5 parts by weight of a sodium lauryl sulfonate and
5 parts by weight of an alkyl-aryl-polyglycol ether.

This mixture is ground to 5–15 μm in a dowelled disc mill or air-jet mill. A good suspension is obtained by adding water to the wettable powder produced in this manner.

DUST 5 parts by weight of the finely ground active substance are thoroughly mixed with
2 parts by weight of a precipitated silicic acid and
93 parts by weight of talc.

POUR-ON-SOLUTION

| | |
|---|---|
| active substance | 30.0 g |
| sodium dioctylsulfosuccinate | 3.0 g |
| benzyl alcohol | 48.0 g |
| peanut oil | 19.8 g |
| | 100.8 g = 100 ml |

The active substance is dissolved in the benzyl alcohol with stirring and if necessary with gentle heating. The sodium dioctylsulfosuccinate and peanut oil are added to the solution, and are dissolved with heating and thorough stirring.

The Examples which follow serve to further illustrate the invention.

EXAMPLE 1

Production of
N-2,6-dimethyl-4-(4'-trifluoromethylphenoxy)-phenyl-N'-tert-butyl-S-methyl-isothiourea 3.1 g of methyl iodide are slowly added dropwise, at a temperature of 50° C., to a solution of 7.3 g of N-2,6-dimethyl-4-(4'-trifluoromethylphenoxy)-phenyl-N'-tert-butylthiourea in 25 ml of dimethylformamide, and the reaction mixture is subsequently stirred for 6 hours at room temperature. The clear yellow reaction solution obtained is stirred into a solution of 300 ml of water and 50 ml of 15% sodium carbonate solution, and the oily precipitate is extracted with methylene chloride. The organic phase is washed with water, dried over $Na_2SO_4$, concentrated by evaporation, and the residue is dried under high vacuum.

There is obtained in this manner the title compound of the formula

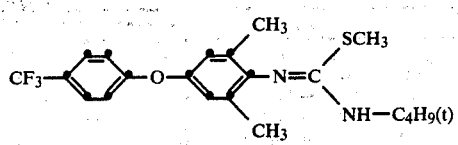

in the form of white crystals having a melting point of 68°–70° C.

The following compounds of the formula I are produced by a process analogous to the described process:

| $R_1$ | $R_2$ | $R_3$ | $R_4$ | $R_5$ | $R_6$ | $R_7$ | Physical data |
|---|---|---|---|---|---|---|---|
| H | H | H | —$CH_3$ | —$CH_3$ | —$CH_3$ | —$C(CH_3)_3$ | $n_D^{20} = 1.5832$ |
| H | H | H | —$CH_3$ | —$CH_3$ | —$nC_4H_9$ | —$C(CH_3)_3$ | $n_D^{20} = 1.5681$ |
| H | H | H | —$CH_3$ | —$CH_3$ | —$CH_3$ | —$CH(CH_3)_2$ | $n_D^{20} = 1.5910$ |
| H | H | H | —$CH_3$ | —$CH_3$ | —$CH_3$ | —$CH_3$ | m.p. 65–67° C. |
| H | H | H | —$CH_3$ | —$CH_3$ | —$CH_3$ | —$C(CH_3)_3$ | (1)m.p. (decomp.) 183° C. |
| H | H | H | —$CH_3$ | —$CH_3$ | —$C_2H_5$ | —$C(CH_3)_3$ | m.p. 71–73° C. |
| H | H | H | —$CH_3$ | —$CH_3$ | —$nC_3H_7$ | —$C(CH_3)_3$ | m.p. 67–69° C. |
| H | H | H | —$CH_3$ | —$CH_3$ | —$CH_3$ | —CH—$C_2H_5$<br>\|<br>$CH_3$ | m.p. 58–60° C. |
| 4-$CH_3$ | H | H | —$CH_3$ | —$CH_3$ | —$CH_3$ | —$C(CH_3)_3$ | m.p. 103–104° C. |
| 4-$OCH_3$ | H | H | —$CH_3$ | —$CH_3$ | —$CH_3$ | —$C(CH_3)_3$ | m.p. 84–85° C. |
| 4-$OCH_3$ | H | H | —$CH_3$ | —$CH_3$ | —$CH_3$ | —$CH(CH_3)_2$ | m.p. 55–57° C. |
| 4-Cl | H | H | —$CH_3$ | —$CH_3$ | —$CH_3$ | —$C(CH_3)_3$ | m.p. 95–97° C. |
| 4-Cl | H | H | —$CH_3$ | —$CH_3$ | —$C_2H_5$ | —$C(CH_3)_3$ | m.p. 79–80° C. |
| 4-Cl | H | H | —$CH_3$ | —$CH_3$ | —$C_2H_5$ | —$C(CH_3)_3$ | (1)m.p. (decomp.) 178–179° C. |
| 4-Cl | H | H | —$CH_3$ | —$CH_3$ | —$nC_3H_7$ | —$C(CH_3)_3$ | m.p. 46–48° C. |
| 4-Cl | H | H | —$CH_3$ | —$CH_3$ | —$nC_4H_9$ | —$C(CH_3)_3$ | $n_D^{20} = 1.5725$ |
| 4-Cl | H | H | —$CH_3$ | —$CH_3$ | —$nC_6H_{13}$ | —$C(CH_3)_3$ | $n_D^{20} = 1.5639$ |
| 4-Cl | H | H | —$CH_3$ | —$CH_3$ | —$CH_3$ | —$CH(CH_3)_2$ | $n_D^{20} = 1.5730$ |
| 4-Cl | H | H | —$CH_3$ | —$CH_3$ | —$C_2H_5$ | —$CH(CH_3)_2$ | $n_D^{20} = 1.5700$ |
| 4-$CF_3$ | H | H | —$CH_3$ | —$CH_3$ | —$CH_3$ | —$C(CH_3)_3$ | (2)m.p. 126–127° C. |
| 4-$CF_3$ | H | H | —$CH_3$ | —$CH_3$ | —$nC_3H_7$ | —$C(CH_3)_3$ | m.p. 53–55° C. |
| 4-$CF_3$ | H | H | —$CH_3$ | —$CH_3$ | —$C_2H_5$ | —$C(CH_3)_3$ | m.p. 71–72° C. |
| 4-$CF_3$ | H | H | —$CH_3$ | —$CH_3$ | —$CH_2$—CH=$CH_2$ | —$C(CH_3)_3$ | m.p. 78–79° C. |
| 4-$CF_3$ | H | H | —$CH_3$ | —$CH_3$ | —$CH_2$—CH≡CH | —$C(CH_3)_3$ | (3)m.p. (decomp.) 170° C. |
| 4-Br | H | H | —$CH_3$ | —$CH_3$ | —$CH_3$ | —$C(CH_3)_3$ | (1)m.p. (decomp.) 187° C. |
| 4-$CF_3$ | H | H | —$CH_3$ | —$CH_3$ | —$CH_3$ | —$nC_{12}H_{25}$ | $n_D^{20} = 1.5288$ |
| 4-$CF_3$ | H | H | —$CH_3$ | —$CH_3$ | —$CH_3$ | —$C(CH_3)_3$ | (3)m.p. (decomp.) 201° C. |
| 4-$CF_3$ | H | H | —$CH_3$ | —$CH_3$ | —$CH_3$ | —$C(CH_3)_3$ | (4)m.p. (decomp.) 183° C. |
| 4-$CF_3$ | H | H | —$CH_3$ | —$CH_3$ | —$CH_3$ | —$CH_2$—$C(CH_3)_3$ | $n_D^{20} = 1.5439$ |
| 4-$CF_3$ | H | H | —$CH_3$ | —$CH_3$ | —$CH_3$ | —$CH_3$ | m.p. 36–38° C. |
| 4-$CF_3$ | H | H | —$CH_3$ | —$CH_3$ | —$CH_3$ | —$CH_2$—$CH(CH_3)_2$ | $n_D^{20} = 1.5465$ |
| 4-$CF_3$ | H | H | —$CH_3$ | —$CH_3$ | —$CH_3$ | —$nC_6H_{13}$ | $n_D^{20} = 1.5429$ |
| 4-$CF_3$ | H | H | —$CH_3$ | —$CH_3$ | —$CH_3$ | cyclopropyl | m.p. 73–74° C. |
| 4-$CF_3$ | H | H | —$CH_3$ | —$CH_3$ | —$CH_3$ | —CH(cyclooctyl, $(CH_2)_7$) | $n_D^{20} = 1.5570$ |
| 3-$CF_3$ | H | H | —$CH_3$ | —$CH_3$ | —$CH_3$ | —$C(CH_3)_3$ | m.p. 77–78° C. |
| 3-$CF_3$ | H | H | —$CH_3$ | —$CH_3$ | —$CH_3$ | —$C(CH_3)_3$ | (4)m.p. (decomp.) 143° C. |
| 4-Cl | 3-Cl | H | —$CH_3$ | —$CH_3$ | —$CH_3$ | —$C(CH_3)_3$ | m.p. 73–75° C. |
| 4-Cl | 3-Cl | H | —$CH_3$ | —$CH_3$ | —$C_2H_5$ | —$C(CH_3)_3$ | m.p. 94–96° C. |
| 4-Cl | 3-Cl | H | —$CH_3$ | —$CH_3$ | —$CH_3$ | —CH—$C_2H_5$<br>\|<br>$CH_3$ | $n_D^{20} = 1.5954$ |
| 4-Cl | H | H | —$CH_3$ | —$CH_3$ | —$CH_2$—$CH(CH_3)_2$ | —$C(CH_3)_3$ | m.p. 60–62° C. |
| 4-$CF_3$ | 2-Cl | H | —$CH_3$ | —$CH_3$ | —$CH_3$ | —$C(CH_3)_3$ | m.p. 64–66° C. |
| 4-$CF_3$ | 2-Cl | H | —$CH_3$ | —$CH_3$ | —$CH_3$ | —$C(CH_3)_3$ | (4)m.p. (decomp.) 205° C. |
| 4-$CF_3$ | 2-Cl | H | —$CH_3$ | —$CH_3$ | —$CH_3$ | cyclohexyl (H) | m.p. 104–106° C. |

-continued

| R₁ | R₂ | R₃ | R₄ | R₅ | R₆ | R₇ | Physical data |
|---|---|---|---|---|---|---|---|
| 4-NO₂ | 2-CF₃ | H | —CH₃ | —CH₃ | —CH₃ | —C(CH₃)₃ | [4]m.p. (decomp.) 195° C. |
| 4-CF₃ | H | H | —CH₃ | H | —CH₃ | —C(CH₃)₃ | m.p. 61-63° C. |
| 4-CF₃ | H | H | —CH(CH₃)₂ | H | —CH₃ | —C(CH₃)₃ | $n_D^{20} = 1{,}5459$ |
| 4-CF₃ | H | H | —CH(CH₃)₂ | H | —CH₃ | —C(CH₃)₃ | [1]m.p. 94-96° C. |
| 4-Cl | H | H | —CH₃ | —CH(CH₃)₂ | —CH₃ | —C(CH₃)₃ | m.p. 99-100° C. |
| 4-Cl | H | H | —CH₃ | —CH(CH₃)₂ | —C₂H₅ | —cyclopropyl | m.p. 86-90° C. |
| 4-Cl | H | H | —CH₃ | —CH(CH₃)₂ | —CH₃ | —C(CH₃)₃ | $n_D^{40} = 1{,}5708$ |
| 4-Cl | H | H | —CH₃ | —CH(CH₃)₂ | —CH₂—C≡CH | —C(CH₃)₃ | m.p. 90-93° C. |
| 4-Cl | H | H | —CH₃ | —C(CH₃)₃ | —C₂H₅ | —cyclopropyl | m.p. 65-70° C. |
| 4-Cl | H | H | —CH₃ | —C(CH₃)₃ | —CH₃ | —cyclopropyl | $n_D^{40} = 1{,}5785$ |
| 4-Cl | H | H | —CH₃ | —C(CH₃)₃ | —CH₂—C≡CH | —(CH₃)₃ | $n_D^{40} = 1{,}5698$ |
| 4-Cl | H | H | —CH₃ | —CH(CH₃)₂ | —CH₃ | —cyclopropyl | $n_D^{40} = 1{,}5850$ |
| 4-CF₃ | 2-Cl | H | —CH₃ | H | —CH₃ | —C(CH₃)₃ | |
| 4-CF₃ | 2-NO₂ | H | —CH₃ | —CH₃ | —CH₃ | —C(CH₃)₃ | |
| 4-CF₃ | H | H | —CH₃ | —CH₃ | —CH₂O—CH₃ | —C(CH₃)₃ | |
| 4-CF₃ | H | H | —CH₃ | —CH₃ | —CH₂—S—CH₃ | —C(CH₃)₃ | |
| 4-CF₃ | H | H | —CH₃ | —CH₃ | —CH₃ | —C(CH₃)₂—C₂H₅ | |
| 4-CF₃ | H | H | —CH₃ | —CH₃ | —CH₃ | —CH(C₂H₅)₂ | |
| 4-CF₃ | H | H | —CH₃ | —CH₃ | —CH₃ | —CH(CH₃)—C₃H₇ | |
| 4-CF₃ | H | H | —CH₃ | —CH₃ | —CH₃ | —nC₈H₁₇ | |
| 4-CF₃ | H | H | —CH₃ | —CH₃ | —CH₃ | —CH₂—CH=CH₂ | |
| 4-CF₃ | H | H | —CH₃ | —CH₃ | —CH₃ | —CH(CH₂)₄ (cyclopentyl) | |
| 4-CF₃ | H | H | —CH₃ | —CH₃ | —cyclopropyl | —C(CH₃)₃ | |
| 4-CF₃ | H | H | —CH₃ | —CH₃ | —C₆H₁₁ (cyclohexyl) | —C(CH₃)₃ | |

[1]salt with 1 mol of HI
[2]salt with 1 mol of HOOC—COOH

[3]salt with 1 mol of 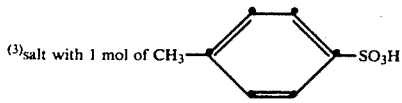

[4]salt with 1 mol of 

EXAMPLE 2

Production of N-2,6-dimethyl-4-(4'-trifluoromethylphenoxy)-phenyl-N'-tert-butyl-thiourea (starting material for Example 1)

16.1 g of 2,6-dimethyl-4-(4'-trifluoromethylphenoxy)-phenylisothiocyanate and 20 g of tert-butylamine are stirred together for 2 hours at 40° C. and subsequently for 5 hours at room temperature. After the reaction solution obtained has been concentrated by evaporation, the residue is taken up in methylene chloride, neutralised with ~5% hydrochloric acid and washed with a small amount of water. After drying over sodium sulfate, the methylene chloride solution is intensively concentrated by evaporation and caused to crystallise by the addition of hexane. The crystals are filtered off with suction, squeezed out and dried. In this manner is obtained the title compound of the formula

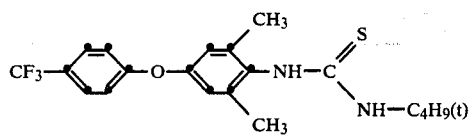

as a pale beige powder having a melting point of 118°–120° C.

The following compounds of the formula II are obtained in an analogous manner:

| $R_1$ | $R_2$ | $R_3$ | $R_4$ | $R_5$ | $R_7$ | Physical data |
|---|---|---|---|---|---|---|
| H | H | H | —$CH_3$ | —$CH_3$ | —$C(CH_3)_3$ | m.p. 161–163° C. |
| H | H | H | —$CH_3$ | —$CH_3$ | —$CH(CH_3)_2$ | m.p. 129–131° C. |
| H | H | H | —$CH_3$ | —$CH_3$ | —$CH_3$ | m.p. 156–158° C. |
| H | H | H | —$CH_3$ | —$CH_3$ | —CH(CH$_3$)—$C_2H_5$ | m.p. 113–114° C. |
| 4-$CH_3$ | H | H | —$CH_3$ | —$CH_3$ | —$C(CH_3)_3$ | m.p. 148–150° C. |
| 4-$OCH_3$ | H | H | —$CH_3$ | —$CH_3$ | —$C(CH_3)_3$ | m.p. 130–132° C. |
| 4-$OCH_3$ | H | H | —$CH_3$ | —$CH_3$ | —$CH(CH_3)_2$ | m.p. 154–156° C. |
| 4-Cl | H | H | —$CH_3$ | —$CH_3$ | —$C(CH_3)_3$ | m.p. 128–129° C. |
| 4-Cl | H | H | —$CH_3$ | —$CH_3$ | —$CH(CH_3)_2$ | m.p. 148–151° C. |
| 4-$CF_3$ | H | H | —$CH_3$ | —$CH_3$ | —$CH_3$ | m.p. 160–162° C. |
| 4-$CF_3$ | H | H | —$CH_3$ | —$CH_3$ | —$C(CH_3)_3$ | m.p. 118–119° C. |
| 4-Br | H | H | —$CH_3$ | —$CH_3$ | —$C(CH_3)_3$ | m.p. 137–139° C. |
| 4-$CF_3$ | H | H | —$CH_3$ | —$CH_3$ | —$nC_{12}H_{25}$ | $n_D^{20} = 1{,}5402$ |
| 4-$CF_3$ | H | H | —$CH_3$ | —$CH_3$ | —$CH_2$—$C(CH_3)_3$ | m.p. 105–107° C. |
| 4-$CF_3$ | H | H | —$CH_3$ | —$CH_3$ | —$CH_2$—$CH(CH_3)_2$ | m.p. 115–116° C. |
| 4-$CF_3$ | H | H | —$CH_3$ | —$CH_3$ | —$nC_6H_{13}$ | m.p. 111–113° C. |
| 4-$CF_3$ | H | H | —$CH_3$ | —$CH_3$ | cyclopropyl | m.p. 130–132° C. |
| 4-$CF_3$ | H | H | —$CH_3$ | —$CH_3$ | —CH(CH$_2$)$_7$ (cyclooctyl) | m.p. 122–124° C. |
| 3-$CF_3$ | H | H | —$CH_3$ | —$CH_3$ | —$C(CH_3)_3$ | m.p. 114–116° C. |
| 3-$CF_3$ | H | H | —$CH_3$ | —$CH_3$ | —$CH_2$—$C(CH_3)_3$ | highly viscous mass |
| 4-Cl | 3-Cl | H | —$CH_3$ | —$CH_3$ | —$C(CH_3)_3$ | m.p. 124–125° C. |
| 4-Cl | 3-Cl | H | —$CH_3$ | —$CH_3$ | —CH(CH$_3$)—$C_2H_5$ | m.p. 97–99° C. |
| 4-$CF_3$ | 2-Cl | H | —$CH_3$ | —$CH_3$ | —$C(CH_3)_3$ | m.p. 136–137° C. |
| 4-$CF_3$ | 2-Cl | H | —$CH_3$ | —$CH_3$ | cyclohexyl | m.p. 129–130° C. |
| 4-$NO_2$ | 2-$CF_3$ | H | —$CH_3$ | —$CH_3$ | —$C(CH_3)_3$ | m.p. 135–136° C. |
| 4-$CF_3$ | H | H | —$CH_3$ | H | —$C(CH_3)_3$ | m.p. 122–124° C. |
| 4-$CF_3$ | H | H | —$CH_3$ | H | —$CH_3$ | m.p. 146–148° C. |
| 4-$CF_3$ | H | H | —$CH(CH_3)_2$ | H | —$C(CH_3)_3$ | m.p. 125–127° C. |
| 4-$CF_3$ | H | H | —$CH(CH_3)_2$ | H | —$CH_3$ | m.p. 180–182° C. |
| 4-$CF_3$ | H | H | —$CH(CH_3)_2$ | H | cyclopropyl | m.p. 116–118° C. |
| 4-Cl | H | H | —$CH_3$ | —$CH(CH_3)_2$ | cyclopropyl | m.p. 143–145° C. |
| 4-Cl | H | H | —$CH_3$ | —$CH(CH_3)_2$ | —$(CH_3)_3$ | m.p. 65° C. |
| 4-Cl | H | H | —$CH_3$ | —$C(CH_3)_3$ | cyclopropyl | m.p. 56–58° C. |
| 4-Cl | H | H | —$CH_3$ | —$C(CH_3)_3$ | —$C(CH_3)_3$ | m.p. 55–59° C. |
| 4-$CF_3$ | 2-Cl | H | —$CH_3$ | H | —$C(CH_3)_3$ | |
| 4-$CF_3$ | 2-$NO_2$ | H | —$CH_3$ | —$CH_3$ | —$C(CH_3)_3$ | |

-continued

| R$_1$ | R$_2$ | R$_3$ | R$_4$ | R$_5$ | R$_7$ | Physical data |
|---|---|---|---|---|---|---|
| 4-CF$_3$ | H | H | —CH$_3$ | —CH$_3$ | —C(CH$_3$)$_3$ | |
| 4-CF$_3$ | H | H | —CH$_3$ | —CH$_3$ | —C(CH$_3$)$_2$—C$_2$H$_5$ | |
| 4-CF$_3$ | H | H | —CH$_3$ | —CH$_3$ | —CH(C$_2$H$_5$)$_2$ | |
| 4-CF$_3$ | H | H | —CH$_3$ | —CH$_3$ | —CH(CH$_3$)—C$_3$H$_7$ | |
| 4-CF$_3$ | H | H | —CH$_3$ | —CH$_3$ | —nC$_8$H$_{17}$ | |
| 4-CF$_3$ | H | H | —CH$_3$ | —CH$_3$ | —CH$_2$—CH=CH$_2$ | |
| 4-CF$_3$ | H | H | —CH$_3$ | —CH$_3$ | —CH(CH$_2$)$_4$ (cyclopentyl) | |

EXAMPLE 3

Insecticidal stomach-poison action: *Spodoptera littoralis, Dysdercus fasciatus* and *Heliothis virescens*

Cotton plants were sprayed with an aqueous emulsion containing 0.05% of the compound to be tested (obtained from a 10% emulsifiable concentrate).

After the drying of the coating, larvae of the species *Spodoptera littoralis* (L$_3$-stage), *Dysdercus fasciatus* (L$_4$) and *Heliothis virescens* (L$_3$), respectively, were settled onto the plants. Two plants were used per test compound and per test species, and an evaluation of the resulting mortality rate was made after 2, 4, 24 and 48 hours. The test was carried out at 24° C. with 60% relative humidity.

Compounds of the formulae I and II according to Examples 1 and 2, respectively, exhibited in the above test a good action against larvae of the species *Spodoptera littoralis, Dysdercus fasciatus* and *Heliothis virescens*.

EXAMPLE 4

Insecticidal stomach-poison action: *Leptinotarsa decemlineata*

The test procedure described in Example 3 was repeated using larvae of the species *Leptinotarsa decemlineata* (L$_3$) and potato plants instead of cotton plants.

Compounds of the formulae I and II according to Examples 1 and 2, respectively, exhibited in this test a good action against larvae of the species *Leptinotarsa decemlineata*.

EXAMPLE 5

Action against plant-damaging acarids: *Tetranychus urticae* (OP-sensitive) and *Tetranychus cinnabarinus* (OP-tolerant)

The primary leaves of *Phaseolus vulgaris* plants were infested, 16 hours before the test for acaricidal action, with an infested piece of leaf from a mass culture of *Tetranychus urticae* (OP-sensitive) and *Tetranychus cinnabarinus* (OP-tolerant), respectively, (tolerance is with respect to diazinon compatibility).

The plants infested in this manner were subsequently sprayed until dripping wet with a test solution containing 400 and 200 ppm, respectively, of the compound to be tested. An assessment was made after 24 hours and again after 7 days, by examination of the imagines and larvae (all mobile stages) under a binocular microscope, of the number of living and dead individuals, respectively.

One plant was used per concentration and per test species. The plants were standing in greenhouse compartments at 25° C. during the course of the test.

Compounds of the formulae I and II according to Examples 1 and 2, respectively, exhibited in this test a good action against *Tetranychus urticae* and *Tetranychus cinnabarinus*.

EXAMPLE 6

Action against ectoparasitic acarids (ticks): *Rhipicephalus bursa* (imagines and larvae), *Anblyomma hebraeum* (♀ imagines nymphs and larvae) and *Boophilus microplus* (larvae—OP-sensitive and OP-tolerant)

The test objects used were larvae (in each case about 50), nymphs (in each case about 25) and imagines (in each case about 10) of the tick species *Rhipicephalus bursa, Amblyomma hebraeum* and *Boophilus microplus*. The test insects were immersed for a short time in an aqueous emulsion or solution containing 0.1, 1.0, 10, 50 and 100 ppm, respectively, of the compound to be tested.

The emulsions or solutions in the test tubes were then absorbed with cotton wool, and the wetted test insects were left in the test tubes treated in this manner.

An evaluation of the mortality rate achieved at each concentration was made after 3 days for larvae and after 14 days for nymphs and imagines.

Compounds of the formulae I and II according to Examples 1 and 2, respectively, exhibited in this test a good action against larvae, nymphs and imagines of the species *Rhipicephalus bursa* and *Amblyomma hebraeum* and also against larvae (OP-resistant and OP-sensitive) of the species *Boophilus microplus*.

EXAMPLE 7

Plant-miticidal leaf-penetration action on *Tetranychus cinnabarinus* and *Panonychus citri*

For the test were used potted bush-bean plants infested with *Tetranychus cinnabarinus*, and potted citrus plants infested with *Panonychus citri*.

The upper side of the leaves of the test plants infested with mites was sprayed with an emulsion preparation containing 400 ppm of the active substance to be tested. After the drying of the sprayed-on coating, the edge of the upper side of a number of infested leaves was bounded with a collar of viscous glue (Pomona Raupenleim) in order to prevent any migration of mites from the underside to the upper side of the leaves.

The treated plants were then kept in a greenhouse at a temperature of 25° to 29° C. Five days after application of the active substance, the mortality rate of the postembryonal and adult stages was determined in order to establish whether a translaminar action, that is to say, a leaf-penetrating action, of the active substance had occurred.

Compounds of the formulae I and II according to Examples 1 and 2, respectively, exhibited a good action in this test.

What is claimed is:

1. A compound of the formula

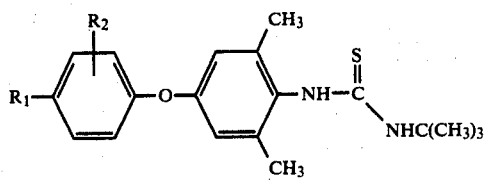

wherein
 $R_1$ is hydrogen, methyl, methoxy, trifluoromethyl, chlorine, bromine or nitro, and
 $R_2$ is hydrogen, chlorine, trifluoromethyl or nitro.

2. A compound according to claim 1 in which $R_1$ is trifluoromethyl or chlorine.

3. A compound according to claim 1 in which $R_2$ is hydrogen or chlorine.

4. A compound according to claim 3 in which $R_1$ is trifluoromethyl or chlorine.

5. The compound according to claim 3 of the formula

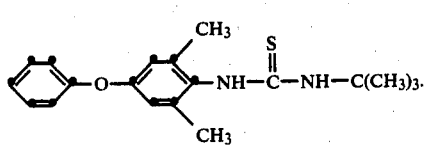

6. The compound according to claim 3 of the formula

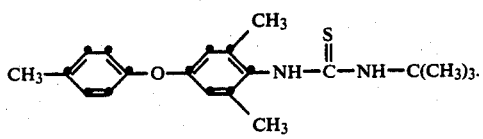

7. The compound according to claim 4 of the formula

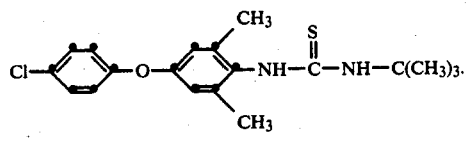

8. The compound according to claim 4 of the formula

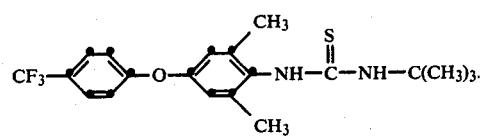

9. The compound according to claim 1 of the formula

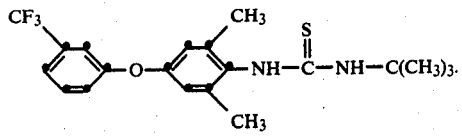

10. The compound according to claim 4 of the formula

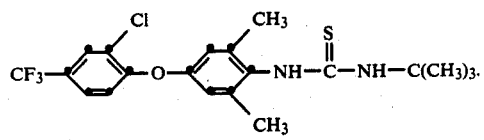

11. An insecticidal and acaricidal composition containing, as active ingredient, an insecticidally or acaricidally effective amount of a compound according to claim 1, and a carrier.

12. A method for combatting insects and acarids which comprises applying thereto an insecticidally or acaricidally effective amount of a compound of the formula

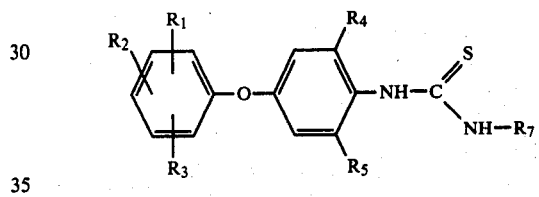

wherein
 each of $R_1$, $R_2$ and $R_3$ is hydrogen, $C_1$-$C_4$ alkyl, methoxy, halogen, trifluoromethyl or nitro,
 $R_4$ is hydrogen or methyl,
 $R_5$ is $C_1$-$C_3$ alkyl, and
 $R_7$ is $C_1$-$C_{12}$ alkyl, $C_3$-$C_5$ alkenyl or $C_3$-$C_8$ cycloalkyl.

13. A method according to claim 12 in which, in the compound,
 each of $R_1$ and $R_2$ is hydrogen, methyl, methoxy, chlorine, trifluoromethyl or nitro,
 $R_3$ is hydrogen,
 $R_4$ is hydrogen or methyl, and
 $R_5$ is methyl.

14. A method according to claim 13 in which $R_2$ is hydrogen or chlorine.

15. A method according to claim 14 in which $R_1$ is in the 4-position.

16. A method according to claim 15 in which $R_1$ is trifluoromethyl or chlorine.

17. A method according to claim 13 in which $R_7$ is tert.-butyl.

18. A method according to claim 12 in which spider mites and insects are combatted and in which the compound is applied to plants infested with said spider mites or insects.

* * * * *